United States Patent [19]

Wagner et al.

[11] Patent Number: 5,503,987
[45] Date of Patent: Apr. 2, 1996

[54] MONOCLONAL ANTIBODIES SPECIFIC FOR SMALL MOIETIES AND METHOD FOR THEIR USE

[75] Inventors: Fred W. Wagner, Walton; Dwane E. Wylie, Lincoln, both of Nebr.; Sheldon M. Schuster, Gainesville, Fla.

[73] Assignee: Board of Regents of the University of Nebraska, Lincoln, Nebr.

[21] Appl. No.: 990,543

[22] Filed: Dec. 14, 1992

Related U.S. Application Data

[63] Continuation of Ser. No. 324,392, Mar. 14, 1989, abandoned.

[51] Int. Cl.$^6$ .......................... G01N 33/547; G01N 33/84; G01N 33/531; C07K 16/44
[52] U.S. Cl. .................. 435/7.94; 435/7.92; 435/240.27; 436/542; 436/543; 530/387.1; 530/388.9; 530/389.8
[58] Field of Search ................................. 435/7.92, 7.94; 436/542, 548; 530/403, 404, 382.1, 388.9, 389.8

[56] References Cited

U.S. PATENT DOCUMENTS

| | | | |
|---|---|---|---|
| 4,281,065 | 7/1981 | Lin et al. ................................. | 435/188 |
| 4,454,106 | 6/1984 | Gansow et al. . | |
| 4,456,691 | 6/1984 | Stark ................................. | 436/547 X |
| 4,472,509 | 9/1984 | Gansow et al. . | |
| 4,474,893 | 10/1984 | Reading . | |
| 4,530,786 | 7/1985 | Dunbar et al. ...................... | 435/961 X |
| 4,608,337 | 8/1986 | Croce . | |
| 4,668,771 | 5/1987 | Kawakami et al. . | |
| 4,677,070 | 6/1987 | Larrick et al. . | |
| 4,681,782 | 7/1987 | Ozkan . | |
| 4,701,408 | 10/1987 | Koestler . | |
| 4,722,892 | 2/1988 | Meares . | |
| 4,731,238 | 3/1988 | Neville et al. . | |
| 4,760,155 | 7/1988 | Heffernan et al. . | |
| 4,760,156 | 7/1988 | Heffernan et al. . | |
| 4,762,781 | 8/1988 | Geffard ................................. | 436/822 X |
| 4,764,359 | 8/1988 | Lemelson . | |
| 4,772,551 | 9/1988 | Hart et al. . | |
| 4,778,752 | 10/1988 | Curtiss et al. . | |
| 4,793,986 | 12/1988 | Serino et al. . | |
| 4,797,473 | 1/1989 | Tarsio et al. . | |
| 4,859,613 | 8/1989 | Lawrence ........................... | 435/7.23 X |

FOREIGN PATENT DOCUMENTS

| | | |
|---|---|---|
| 028795 | 5/1981 | European Pat. Off. . |
| 043285 | 1/1982 | European Pat. Off. . |
| 149405 | 7/1985 | European Pat. Off. . |
| 0173629 | 4/1986 | European Pat. Off. . |
| 0235457 | 9/1987 | European Pat. Off. . |
| 0286323 | 10/1988 | European Pat. Off. . |
| 0261416 | 11/1988 | European Pat. Off. . |
| 2561660 | 9/1985 | France . |
| 3515901 | 11/1986 | Germany . |
| 55-99072 | 7/1980 | Japan . |
| 58-38860 | 3/1983 | Japan . |
| 62-051699 | 3/1987 | Japan . |
| WO86/02736 | 5/1986 | WIPO . |

OTHER PUBLICATIONS

L. Treagan, *Biol. Trace Element Res.*, 1, 141–148 (1979).
M. Verhoeyan et al., *Science*, 239, 1534–1536 (1988).
R. J. P. Williams, *Nature*, 332, 393 (1988).
"Stability Constants of Metal Complexes A: Chelating Agents," at 404–405.
S. C. Stinson, *Chem. Eng. News*, 30–33 (Oct. 19, 1987).
A. Tramontano et al., *Science*, 234, 1566–1569 (1986).
S. J. Pollack et al., *Science*, 234, 1570–1573 (1986).
D. T. Reardan et al., *Nature*, 316, 265–268 (1985).
I. Rubinstein et al., *Nature*, 332, 426–429 (1988).
M. Naito, *Chem. Abstracts*, 95, 92911k (1980).
A. D. Napper et al., *Science*, 237, 1041–1043 (1987).
F. Nielsen Kudsk, *Chem. Abstracts*, 82, 11898t (1973).
Masterson & Slowiriski, *Chemical Principals*, (W. B. Saunders, 1969) at 482–487.
H. Matsui et al., *J. Biol. Chem.*, 260, 4174–4179 (1985).
C. F. Meares, "Attaching Metal Ions to Antibodies" 339–352 (1987).
F. Lindgarde & O. Zettervall, *Scand. J. Immunol.*, 3, 277–285 (1974).
L. Magos et al., *Chem. Abstracts*, 90, 98118a (1978).
R. J. Massey, *Nature*, 328, 457–458 (1987).
K. Kenmotsu, *Chem. Abstracts*, 13, 07669m (1984).
D. C. Langan et. al., *J.A.D.A.*, 115, 867–880 (1987).
R. A. Lerner & A. Tramontano, *T.I.B.S.*, 12, (no page nos.) (1987).
F. Forghieri et al., *Aust. J. Chem.*, 36, 1125–1132 (1983).
J. F. Hainfeld, *Nature*, 333, 281–282 (1988).
M. Karin, *Cell*, 41, 9–10 (1985).
M. Caise, *Methods in Enzymology*, 92 (Academic Press, 1983) at 445–458.
P. Cenini, *Comp. Biochem. Physiol.*, 81c, 213–217 (1985).
M. C. Cress & T. T. Ngo, *ABL*, 16–19 (Feb., 1989).
L. Wide & J. Porath, *Bio Chem. Bio Phys. Acta.*, 130, 257–260 (1966).
B. L. Baker & D. E. Hultquist, *J. Biol. Chem.*, 253, 8444–8541 (1978).
R. M. Baum, *Chem. and Eng. News*, 19–20 (Jan. 23, 1989).
V. P. Butler and S. M. Beiser, *Advances in Immunol.*, 17 255–310 (1973).
V. P. Torchilin et al., *Hybridoma*, 6, 229–240 (1987).
C. F. Meares, *Nucl. Med. Biol.*, 13, 311–318 (1986).
*Dialog Information Services*, File 35: Dissertation Abstracts Online 1861–Jun. 90, Dialog acession No. 894111, Dayton T. Reardan: "Metal Selective Antibodies and Bifunctional Metal Chelates" vol. 46/07–B of Dissertation Abstracts International, p. 2326, 254 pages.

(List continued on next page.)

*Primary Examiner*—Michael P. Woodward
*Attorney, Agent, or Firm*—Merchant, Gould, Smith, Edell, Welter & Schmidt

[57] ABSTRACT

The invention is directed to monoclonal antibodies which immunoreact with bare small moieties such as metallic cations and small organic molecules, the hybridomas for production of the monoclonal antibodies, immunogen compounds for developing the hybridomas, and methods for use of the monoclonal antibodies.

28 Claims, 3 Drawing Sheets

OTHER PUBLICATIONS

*Science*, vol. 243, 3 Mar. 1989, Brent L. Iverson et al.: "Sequence–specific Peptide Cleavage Catalyzed by an Antibody", pp. 1184–1188.

*Methods of Enzymology*, vol. 70, 1980, Immunochemical Techniques, Part A, Helen Van Vunakis: "The Preparation of Antigenic Hapten–Carrier Conjugates: a Survey", pp. 85–104.

*Monoclonal Antibodies and New Trends in Immunoassays*, 1984, Ch. A. Bizollon et al.: "Monoclonal Antibodies to Haptens", pp. 53–58.

Kabakoff in *Enzyme Immunoassay*, Maggio, E. T., ed. CRC Press: Florida, pp. 78–88, 1980.

Fuhr et al. *J. Am. Chem. Soc.* 95:6944, 1973.

Kohler et al. Nature 256:495, 1975.

N. Yamamoto et al., *J. Immunol. Methods*, 22, 309–317 (1978).

Hawley's *Condensed Chemical Dictionary*, p. 748 (11th Edition).

Yelton et al., "Use of Monoclonal Anti–mouse Immunoglobulin to Detect Mouse Antibodies", *Hybridoma*, 1:5–11 (1981).

Spitalny et al., "Monoclonal Antibody to Murine Gamma Interferon Inhibits Lymphokine–Induced Antiviral and Macrophage Tumoricidal Activites", *J. Exp. Med.*, 159:1560–1565 (1984).

Ohara et al., "Production of a monoclonal antibody to and molecular characterization of B–cell stimulatory factor–1", *Nature*, 315:333–336 (1985).

Gigliotti et al, "Reproducible Production of Protective Human Monoclonal Antibodies by Fusion of Peripheral Blood Lymphocytes with a Mouse Myeloma Cell Line", *J. Infect. Dis.*, 149:43–47 (1982).

Wade et al., "Engineering Metal Coordination Sites into the Antibody Light Chain", *J. Am. Chem. Soc.*, 115:4449–4456 (1993).

Van Regenmortel, "Which structural features determine protein antigenicity?" TIBS 11:36–39 (1986).

Buenafe et al., abstract of "Combining Site Specificity of Monoclonal Antibodies to the Organophosphate Hapten Soman", *Mol. Immunol.* 24:401 (1987).

Chedid et al., abstract of "Specific Absorption with Monoclonal Antibodies to Muramyl Dipeptide of the Pyrogenic and Somnogenic Activities of Rabbit Monokine", *Proc. Natl. Acad. Sci. USA*, 81:5888–91 (1984).

Delaage et al., "Chapter A: Monoclonal Antibodies to Haptens", *Monoclonal Antibodies and New Trends in Immunoassays*, A. Bizollon editor, at pp. 52–59 (1984).

Erlanger, "The Preparation of Antigenic Hapten–Carrier Conjugates: A Survey", *Methods in Enzymology*, 70:85–104 (1980).

Ohnishi et al., "Water–Soluble Carrier Proteins Having Carboxyl Spacer Groups", *Chem. Pharm. Bull.*, 33:2871–2876 (1985).

Lewis et al., "Hypercupremia Associated with a Monoclonal Immunoglobulin", *J. Lab. Clin. Med.*, 88:375–388 (1976).

Shirakawa et al., "The Existence of Specific Antibodies to Cobalt in Hard Metal Asthma", *Clinical Allergy*, 18:451–460 (1988).

Shirakawa et al., "Occupational Asthma from Cobalt Sensitivity in Workers Exposed to Hard Metal Dust", *Chest*, 95:29–37 (1989).

Yelton et al., "Use of Monoclonal Anti–Mouse Immunoglobulin to Detect Mouse Antibodies", *Hybridoma*, 1:5–11 (1981).

Friguet et al., "Measurements of the True Affinity Constant in Solution of Antigen–Antibody Complexes by Enzyme–Linked Immunosorbent Assay", *J. Immunol. Methods*, 77:305–319 (1985).

Gillespie et al., *Chemistry*, Allyn and Bacon, Inc. (1986) at pp. 767–769.

*Immunology: The Science of Self–Nonself Discrimination*, Jan Klein, editor; John Wiley & Sons, NY, publisher; at p. 348 (1972).

Pinekard, "Dialysis and Preparation of Hapten Conjugates" in *Handbook in Exp. Immunology*, 3rd ed., Blackwell Scientific, publishers (1978) at pp. 17.7 to 17.23.

Wylie et al., "Monoclonal Antibodies Specific for Mercuric Ions", *Proc. Natl. Acad. Sci.–USA*, 89:4104–4108 (1992).

S. Fazekas de St. Groth, "Chapter 1: The Quality of Antibodies and Cellular Receptors", *Immunological Methods*, I. Lefkovits and B. Pernis, editors; Academic Press (1979).

MONOCLONAL ANTIBODIES SPECIFIC FOR SMALL MOIETIES AND METHOD FOR THEIR USE

This application is a continuation of application Ser. No. 07/324,392 filed Mar. 14, 1989, now abandoned.

TECHNICAL FIELD

This invention relates to: novel methods for detecting, removing, neutralizing or adding minute quantities of small moieties such as metallic cations and small organic molecules; monoclonal antibodies that are immunoreactive with the small moieties; and hybridomas for production of the monoclonal antibodies.

BACKGROUND OF THE INVENTION

Small chemical moieties can and often do affect the environment and biological systems. These effects become astounding when it is realized that minute quantities of small moieties are involved. Moreover, the presence or absence of low concentrations of small moieties in the environment can have long term consequences. Fluoridated water and lead in gasoline bear witness. Minute quantities of metallic cations and small organic molecules can regulate, influence, change or toxify the environment or biological systems.

The detection, removal, addition or neutralization of such minute quantities constitutes a focal point for continued research in many fields. For example, many efforts have been made to detect and remove minute, toxic amounts of heavy metal ions such as cadmium from the environment. The efforts often have not been successful or economical for widespread application. On the other hand, minute concentrations of other heavy metals are important for the proper function of biological organisms. Zinc, for example, plays a major role in wound healing. The function of magnesium in plant photosynthesis is another.

Small moieties also exhibit dual roles. Mercury is used in diuretics, topical anti-bacterial agents, skin antiseptics, ointments, and in chemical manufacturing operations. Yet when ingested by mammals, such as from drinking water, it is highly toxic in very small amounts. Hence, detection and quantification of minute concentrations of heavy metals in drinking water and other media would serve exploratory, safety and regulatory goals.

Small organic molecules such as cleaning fluids (e.g. trichloroethylene), pesticides and herbicides have small business, agricultural and industrial applications. The former are used in processing, formulating, cleaning and purifying while the latter retard infestation by vermin, insects and undesired plants. However, these molecules also find their way into ground water and subsequently contaminate water used for consumption, agricultural and industrial purposes. Hence, efficient and accurate identification of minute concentrations of small organic molecules in drinking water or other media would be an important step toward their control.

Cosmetic formulations, perfumes, and other proprietary products often contain minute levels of certain small organic compounds. The appropriate selection and mixture of these compounds is the secret of the perfumer's art. Hence, determination of the concentrations and identities of these compounds could serve as a means for cosmetic control or for cosmetic design.

Many foods contain minute quantities of small organic compounds. These compounds contribute to the flavor notes and odor of the foods. For example, ethyl butyrate and limonene contribute to the fresh flavor notes so characteristic of freshly squeezed orange juice. Hence, determination of the concentrations and identities of such compounds within foods and the isolation and purification of the same would help advance food design and screening.

Removal of minute quantities of small moieties from biological or inanimate systems carries many implications. Sea water contains minute concentrations of gold and platinum. Economic removal and refining of these noble metals from sea water could be rewarding. Nuclear contaminants such as radioactive strontium, cobalt and others can endanger the population. Selective removal of these radioactive isotopes from the fluids and tissues of people so contaminated could avoid radiation sickness.

It would, therefore, be highly desirable to identify and control minute quantities of helpful or harmful small moieties in aqueous biological or inanimate systems. In most contexts, however, the detection, removal, addition or neutralization of small moieties is a difficult and expensive and often unfeasible if not impossible task. Contaminants often mimic the small moieties. Measurement interference will result. Moreover, the detection methods employed today are usually not sufficiently sensitive at the minute quantities under consideration here. Consequently, it is desirable to develop reliable and economic methods for accurately identifying and controlling minute quantities of small moieties in aqueous systems.

Antibodies would seem to be uniquely suited for this task. Their high degree of specificity for a known antigen would avoid the interference caused by contaminants. Their sensitivity in the picomolar or lower range would accurately and efficiently target and detect the minute levels.

Monoclonal antibodies, of course, come to mind as especially suited agents for practice of this technique. Since Kohler and Milstein published their article on the use of somatic cell hybridization to produce monoclonal antibodies (*Nature* 256:495 (1974)), immunologists have developed many monoclonal antibodies which strongly and specifically immunoreact with antigens.

Notwithstanding this suggestion, the conventional understanding about immunology teaches that antibodies against small moieties cannot be developed. The mammal immunization step, which is key for the production of monoclonal antibodies, requires a molecule that is large enough to cause antigenic reaction. Medium sized molecules (haptens), which are not of themselves immunogenic, can induce immune reaction by binding to an immunogenic carrier. Nevertheless, immunologists view small molecules such as metallic cations and small organic molecules as not large or structurally complex enough to elicit an antibody response. One theory appears to hold that electron rich rings such as those associated with benzene and carbohydrates are needed at a minimum to cause immunogenicity. V. Butler, S. Beiser, *Adv. Immunol.*, 17, 255 (1973). The molecular size and complexity of an inorganic or organic small moiety is thought to be insufficient for eliciting an antibody response. To date, therefore, no monoclonal antibodies which immunoreact with small moieties per se have been reported in the literature.

Several immunologists have reported production of monoclonal antibodies to metallic ion chelates. For example, in U.S. Pat. No. 4,722,892, monoclonal antibodies are disclosed which immunoreact with a complex of a chelating agent, such as ethylene diamine tetracetate (EDTA), and a heavy metal such as indium. In EPO Patent Application 0235457, monoclonal antibodies that immunoreact with a chelate of gold cyanate and carbonate coating are disclosed. In these instances, however, the monoclonal antibodies bind with the metal chelate complex rather than the bare metallic ion itself. Disadvantages of these methods include: the complicated reagents involved in detection, lack of simple tests that discriminate among antigens, cross-reactivity with chelates of other antigens and cross-reactivity with the chelate itself.

Other instances of monoclonal antibody combinations with metals involve metal tags. The metal chelates are bound to the antibody at a site remote from the antigen binding site or sites. The metal or metal chelate is not the antigen. Instead, it is a tag to indicate the presence of the monoclonal antibody when it reacts with its specific antigen. See for example, V.P. Torchilian et al., *Hybridoma*, 6, 229 (1987); and C. F. Meares, *Nuclear Medical Biology*, 13, 311–318 (1986).

It is therefore, an object of the invention to develop monoclonal antibodies that immunoreact with small moieties per se. It is another object of the invention to develop methods for detecting or neutralizing small moieties within, adding small moieties to, or removing small moieties from biological or inanimate systems through the use of the monoclonal antibodies. Further objects include development of hybridomas which produce the monoclonal antibodies and development of immunogen compounds for generation of antibody reactivity to the small moieties. Yet another object is the development of monoclonal antibodies that are capable of discriminating very similar small moieties.

SUMMARY OF THE INVENTION

These and other objects are achieved by the present invention which is directed to monoclonal antibodies for immunoreaction with small moieties. The invention is as well directed to hybridomas which produce the monoclonal antibodies and to immunogen compounds of the small moieties which cause development of the appropriate mammalian antibody response. The invention is further directed to methods for detecting, removing, adding, or neutralizing the small moieties in biological and inanimate systems through the use of the monoclonal antibodies.

The advantages of the invention include among others: the lack of complication by additional reagents, a high discrimination against similar antigenic materials, lack of cross-reactivity with similar antigenic materials, and lack of cross-reactivity with test reagents.

The monoclonal antibody of the invention immunoreacts with a small moiety per se. The state of the small moiety during this immunoreaction is one of non-coordination with any other substance; in other words, it is bare or exposed.

Preferably, the monoclonal antibody exhibits a substantially high degree of specific immunoreactivity toward the small moiety. Also preferably, the monoclonal antibody is a member of the immunoglobulin G, A or E classes and has an association constant for the small moiety that is about 10,000 fold greater than the association constant for the immunogen compound without the small moiety. Also preferably, the monoclonal antibody is immunospecific for a particular member of a group of very similar small moieties. The monoclonal antibody will exhibit a relative association constant for such a particular small moiety that is about 10,000 fold greater than that for the other small moieties of such a group.

The hybridoma of the invention, which produces the monoclonal antibody, is formed from immune cells that are specific for the small moiety. The formation is accomplished by fusion of an immortal mammal cell line and mammal immune cells from a second mammal previously immunized with the immunogen compound which contains the small moiety. Selection of the appropriate hybridoma is determined by cross-screening the secreted monoclonal antibody against the small moiety and against controls which incorporate the small moiety or very similar congeners.

The immunogen compound of the invention is composed of a biopolymer carrier, a spacer arm covalently bonded to the carrier and the small moiety which is coordinated or covalently bonded to the spacer arm. The spacer arm is semi-rigid and has at least one small moiety coordination site. This arrangement maintains the small moiety in at least a partially exposed state and prevents substantially complete inclusion or chelation of the small moiety by spacer arm and/or carrier.

The biopolymer carrier may be a polysaccharide, a synthetic polyamide or preferably a protein. Preferred classes include blood or tissue sera proteins.

The spacer arm is no more than about 25 atoms in length. It is composed of one of three classes: an oligopeptide, an aliphatic compound or an aliphatic fragment. The first two are each substituted with no more than about 2 pendent Lewis acid or base groups, and a coupling group for forming a covalent bond with the protein carrier. The latter is substituted by a coupling group for forming a covalent bond with the protein carrier, and a carboxylic acid, aldehyde, hydroxyl, mercapto, amine or other group adapted for carbon-carbon bonding with, or covalently bonded to the small moiety. For each class of spacer arm, the coupling group is an amine, carboxylic acid, aldehyde, hydroxyl or mercapto group. The latter class of spacer arm is appropriate when the small moiety is an organic compound.

A preferred spacer arm for metallic cations is an oligopeptide or aliphatic compound having no more than about 2 pendent Lewis base groups wherein the deformation of the electron shell of the Lewis base group is approximately of the same character as the deformation of the electron shell of the metallic cation. Especially preferred Lewis base groups for transition elements and the heavy metals are those containing sulfur. Especially preferred are oligopeptides such as glutathione and cysteine, mercapto ethanol amine, dithiothreitol, amines and peptides containing sulfur and the like.

The small moiety has a molecular size of no more than about 15 to 20 angstroms in length. Included are metallic cations and linear or branched aliphatic organic molecules having a molecular size of no more than about 15 atoms in length. Organic small moieties having aromatic rings can as well be detected, neutralized, added or removed according to the invention.

The metallic cations are derived from metals such as aluminum, lithium, boron, gallium, galenium, arsenic, period four transition metals, and period five, six and seven metals, transition elements and inner transition elements. Metallic cations of special mention as the small moiety include those derived from zinc, lead, cadmium, bismuth, cobalt, arsenic, chromium, copper, nickel, strontium and mercury.

Organic compounds of special mention as the small moiety include aliphatic compounds, linear organic compounds, small peptides, saccharides, fats, linear organic compounds which may be substituted by polar groups, pesticides, herbicides, toxic halogenated organic compounds and aromatic compounds. The organic compounds may be optionally substituted by halogens and other groups such as esters, ethers, hydroxyls, amides, sulfides, sulfones, sulfates, sulfhydryls, nitros, nitriles and the like.

The methods according to the invention utilize the monoclonal antibody for detection, removal, neutralization or addition of the small moiety respectively in, from, within or to a liquid or gaseous medium. These methods utilize features such as monoclonal antibody immobilization, small moiety immobilization, competitive binding, and means employing an oscillating probe, a micromagnetic probe and other physiochemical methods used to monitor antigen-antibody interactions.

Methods for detection that are based upon small moiety immobilization indicate the presence of the small moiety-monoclonal antibody complex by known immunologic assay techniques. In a first step, the small moiety is coordinated with an immobilized spacer arm for the small moiety. The spacer arm can be any of the foregoing that will hold the small moiety in at least a partially exposed state. It need not be the same spacer arm of the immunogen compound used to develop the monoclonal antibody. Non-immobilized materials are then removed from the mixture holding the immobilized spacer arm-small moiety. Addition of the monoclonal antibody, removal of uncomplexed monoclonal antibody and immuno-assay complete the steps for this detection method.

Methods for detection that are based upon an immobilized monoclonal antibody utilize a radioactive version of the small moiety or a similar tagged form thereof. Such tags include fluorescent, colorimetric and other spectrally active groups that can be coordinated or bonded to the small moiety like the spacer arm. A preferred tag is a spacer arm containing a spectrally active group. First, the immobilized monoclonal antibody is saturated with the tagged small moiety. After removal of the non-immobilized components, an aliquot of the unknown small moiety is added. It displaces a portion of the bound, tagged small moiety and measurement of that amount displaced will determine the concentration of unknown moiety.

Methods for detection that are based upon an oscillating probe utilize either an immobilized spacer arm for the small moiety or preferably immobilized monoclonal antibodies. This method measures the change in frequency of an oscillating surface as a function of the change in weight of that surface due to the binding of the non-immobilized small moiety or monoclonal antibody. In the preferred method the monoclonal antibodies are immobilized on the surface of a high frequency oscillating probe. The probe is placed into a medium containing an unknown quantity of small moiety. Binding of the small moiety to the immobilized monoclonal antibody will change the oscillation frequency of the probe. Hence, the degree of change will indicate the level of small moiety present.

When the small moiety is a metal ion in an aqueous medium, an especially preferred method for detection utilizes an oligopeptide having reactive sulfhydryl group(s) capable of coordinating with the metal ions. The oligopeptide and the monoclonal antibody specific for the metal ion unknown are added to the aqueous medium. The medium then is assayed for the presence of metal ion-monoclonal antibody complex. The interaction of the antibody with the metal ion is independent of the order of addition of the reactants and is independent of the identity of the oligopeptide.

In an especially preferred version of this method, a fixed support is utilized. Here, either the oligopeptide or the monoclonal antibody is immobilized on the fixed support. The method is then conducted as related above.

The invention, in addition, contemplates methods for small moiety removal from, small moiety neutralization within or small moiety addition to biological or inanimate systems. For all methods, an effective amount of the monoclonal antibody is combined in some fashion with at least part of the system. Pursuant to the removal method, immunoconjugated monoclonal antibody-small moiety is removed by separation means such as immunoprecipitation, immobilization, chromatography, filtration and the like. Pursuant to the neutralization method, the immunoconjugated monoclonal antibody-small moiety remains in the system until it is removed by non-specific means. Pursuant to the addition method, the immunoconjugated antibody-small moiety also remains in the system and the small moiety is actively incorporated or otherwise used therein.

When the system participating in the foregoing methods is biological, the monoclonal antibody may be combined with a pharmaceutically acceptable carrier. Preferably, the monoclonal antibody will not of itself cause an undesirable immune response of the biological system. The biological systems contemplated according to the invention include unicellular organisms, multicellular simple organisms, cellular component systems, tissue cultures, plants and animals, including mammals.

The present invention also contemplates methods for removing heavy metallic cations or radioactive compounds from human fluids such as blood, serum or lymph by utilization of immobilized monoclonal antibodies. An extracorporeal shunt placed in the patient permits removal of the body fluid and its reintroduction. Passing the body fluid extracorporeally through a bed of immobilized monoclonal antibody accomplishes the desired removal.

When a method for adding a monoclonal antibody-small moiety conjugate to a biological or inanimate system is contemplated, the monoclonal antibody will preferably be bifunctional. The second binding site of the monoclonal antibody will be reactive with a selected component of the system. That component may be a complex organic molecule, living cells, selected tissue of a tissue culture or a selected tissue of an animal. In this method, the small moiety will exert a desirable action upon the component of the biological or inanimate system targeted.

The present invention also contemplates a kit for assaying the presence and quantity of small moiety in a biological or inanimate system. The kit includes aliquots of monoclonal antibodies in the appropriate buffer, as well as a fixed support for absorption of the small moiety, washing solutions, reagents such as enzyme substrates, and antisera conjugated to a detectable substrate which antisera are specific for the monoclonal antibodies.

DETAILED DESCRIPTION OF THE INVENTION

Monoclonal antibodies of the present invention are key to the development of methods for detecting, adding, neutralizing or removing minute quantities of small moieties. Until the present invention, it was not possible to produce antibodies to small moieties such as exposed metal cations per se or to small linear organic compounds, especially those without rings. The novel techniques for incorporating small moieties into immunogen compounds and for administering these immunogen compounds to immune cell hosts allow production of the desired, immunospecific monoclonal antibodies according to the invention. These methods are believed to constitute an advancement in the understanding of immunology.

Although not intended as a limitation of the invention, it is now believed that mammalian immunogenic reactivity can be elicited by small moieties. While they are smaller than the recognized epitopal size of approximately 20–25 angstroms, the small moieties nevertheless can epitopally bind.

Notwithstanding these beliefs, the invention contemplates monoclonal antibodies to small moieties, the hybridomas therefor, the immunogen compounds for carrying the small moieties and inducing immunogenicity, and methods for detection, addition, neutralization or removal of small moieties using the monoclonal antibodies.

Monoclonal Antibodies

The monoclonal antibodies of the invention are mammalian immunoglobulin proteins which have strong affinity constants for specific small moieties. Preferably, they are from the IgG, IgA and IgE classes of immunoproteins. They are characterized by selective immunoreactivity with a particular small moiety and a substantially lower immunoreactivity with other similarly structured small moieties. Preferably, the monoclonal antibodies have an association constant for the selected small moiety that is at least about 10,000 fold greater than the association constant for the similarly structured small moiety. With respect to heavy metal cations, the especially preferred IgG class of monoclonal antibodies of the present invention exhibit discriminatory dissociation constants of about $10^{-6}$ to about $10^{-12}$. One example is a monoclonal antibody of the IgG class which is produced by hybridoma having BN No. 4A10B4 and ATCC deposit No. HB 10381 (deposited Mar. 13, 1990), and has a dissociation constant for mercury cation of less than about $10^{-9}$ but does not bind cadmium, copper, zinc, lead, nickel and cobalt cations to any appreciable extent. Another example is a monoclonal antibody of the IgG class which is produced by hybridoma having BN NO. 3H7G5 and ATCC deposit No. HB 10383 (deposited Mar. 13, 1990), and has a dissociation constant for lead cation of less than about $10^{-9}$ but does not bind cadmium, copper, zinc, mercury, nickel and cobalt cations to any appreciable extent.

With respect to small organic molecules, the IgG, IgA and IgE classes of monoclonal antibodies of the present invention exhibit discriminatory dissociation constants of at least about $10^{-6}$. Examples include monoclonal antibodies that are selective for trichloroethylene, polychlorinated biphenyl, ethyl mercaptan, chlordane and hydrophobic residues.

Immunogen Compounds

The immunogen compounds for generation of the specific immunogenicity of the monoclonal antibodies are based upon the hapten-carrier concept. The present invention, however, broadens this concept so that the hapten is coordinated at the end of a spacer arm covalently bonded to the carrier. The spacer arm is adapted so as to be semi-rigid and to hold the small moiety in an exposed position relative to the carrier. This arrangement is also adapted to maintain the small moiety in a substantially exposed and preferably, essentially completely exposed state. These factors combine substantially to avoid chelating, encovering or inclusion of the small moiety by the spacer arm and/or the carrier.

The spacer arm, as characterized above, may be an oligopeptide, an aliphatic compound, or an aliphatic fragment. In the latter two instances, the aliphatic compound or fragment may be covalently bonded to the carrier by means of a Schiff base reaction with an aldehyde group, an amide reaction with an amine or carboxylic acid group using a peptide activator such as carbodiimide, acid chloride and the like, an ester reaction with a hydroxyl or carboxylic acid group using a Schotten Bauman reaction, or azide or acid catalysis reaction, a sulfide reaction using a sulfide coupling agent, or other known coupling reactions for joining organic molecules to proteins. See for example Kabat, E. A., *Structural Concepts In Immunology and Immunochemistry*, 2nd Ed., Holt, Rinenary and Winston, New York, 1976 (a review text of such methods) and Jaime Eyzaguirre, *Chemical Modification of Enzymes: Active Site Studies*, John Wiley & Sons (1982), the disclosures of which are incorporated herein by reference. The oligopeptide, aliphatic compound or fragment will contain backbone groups which provide semi-rigidity to the spacer arm. Preferred groups for developing this semi-rigidity include peptide bonds, olefin bonds, olefinic conjugated systems, ester groups and enone groups. Optionally, and especially where immunogenicity of the small moiety appears difficult to generate, one or more aromatic rings can be incorporated into the spacer arm to stimulate the development of an immune response.

In general, the oligopeptide spacer arm has the following formula:

wherein X is a coupling group that will bond to the carrier, R is one or more amino acid residues and Y is the Lewis Acid or Base group(s) for small moiety coordination.

In general, the aliphatic compound or fragment spacer arm has the following formula:

wherein X is a coupling group that will bond to the carrier, Q is a semirigid aliphatic moiety containing ester, amide, keto, olefin or aromatic groups and the like, and Z is a Lewis acid or Base group(s) for small moiety coordination or is a group that will form a covalent carbon bond with an organic small moiety to form a mimic.

Preferably, an oligopeptide or aliphatic compound is used as the spacer arm when the small moiety is a metallic cation. In this instance, the pendent Lewis base groups will preferably be positioned at the spacer arm end remote from the carrier. These Lewis base groups function as the coordination site or sites for the metal cation. It is preferable that the deformability of the electron shells of the Lewis base groups and the metal cations be approximately similar. Accordingly, sulfur groups can serve as the Lewis base groups when the metal cations are transition metals or inner transition elements. Nitrogen containing groups are preferably employed as the Lewis base groups when aluminum, lithium, boron, strontium, magnesium, and other small atomic diameter metallic cations function as the small moieties.

When the small moiety is a small organic molecule, the spacer arm will be covalently bonded or bondable to it. The resulting compound will be a spacer arm-small moiety mimic. The semi-rigidity of the spacer arm portion of the mimic holds the small moiety portion in a position exposed and remote from the carrier. Preferred classes of spacer arm mimics for this aspect of the invention include aliphatic carboxylic acids, amines and aldehydes having semi-rigid backbones and having tails which duplicate the structure of the small moiety. For example, when the small moiety is trichloroethylene, an appropriate spacer arm-mimic is N-(trichloroacryoyl) glycine. In general, the structure of the spacer arm-mimic is as follows:

wherein X and Q are defined as given above, A is a bond or group attaching $M_s$ to Q and $M_s$ represents the organic molecule which is acting as the small moiety.

The spacer arm mimic can as well act as a tagged small moiety. It participates in the methods for detection that employ immobilized monoclonal antibody. Spectrally active groups can be joined to the spacer arm mimic or incorporated therein to provide a discernable, detectable signal. Such groups include fluorescent groups, colorimetric groups, U.V. groups and others known in the art.

The carrier of the immunogen compound is a large biopolymer that is known to participate in the development of hapten antigenicity. Blood serum proteins, amylopectins, polysaccharides, fetal serum components, biologically acceptable natural and synthetic proteins and polyamides such as polyglycine can serve as the carriers. Preferred carriers include serum and tissue proteins. Examples are keyhole limpet hemocyanin (KLH) and bovine serum albumin (BSA). Other examples include ovalbumin and chicken gamma globulin. These carriers have sites for coordinate bonding of the spacer arm. Such sites are preferably populated by amine groups, carboxylic acid groups, aldehyde groups and/or alcohol groups.

Production of Hybridomas

The production of hybridomas according to the invention generally follows the Kohler, Milstein technique. Many of the small moieties, however, toxify the mammalian system being used as a source of immune cells. This effect makes it important to determine the highest allowable dose of small moiety and/or immunogen compound that can be used over a substantially long period of time without killing the host.

Pursuant to the Kohler, Milstein technique, immunization of the mammalian host is accomplished within this dose parameter by subcutaneous or intraperitoneal injection of the immunogen compound in adjuvant. Administration is repeated periodically and preferably for at least four injections. Three days before the spleen is removed, a priming injection of immunogen compound is again administered.

After their separation, the spleen cells are fused with immortal mammal cells such as mouse myeloma cells using the techniques outlined by Kohler and Milstein. Polyethylene glycol (PEG) or electrical stimulation will initiate the fusions.

The fused cells are then cultured in cell wells according to culture techniques known in the art. Cellular secretions in the culture medium are tested after an appropriate time for the presence of the desired cellular products.

Selection Technique

The selection technique for identifying the appropriate monoclonal antibody is an important aspect for determining the immunospecificity desired according to the invention. The selection techniques according to the invention call for determining the binding affinity of the hybridoma cellular products against the small moiety and against cross-reactive controls. In particular, hybridoma culture fluid is tested in screening assays against the small moiety, the carrier, the carrier-spacer arm product and the immunogen compound as well as optionally against the spacer arm-small moiety coordinate. In instances where the small moiety is an organic compound, cross-reactivity controls against a spacer arm-mimic wherein the mimic tail includes the backbone of the small moiety but not the carbon substituents of the small moiety, may be included. This will eliminate cross-reactivity with the carbon backbone of the spacer arm-mimic.

Screening assays can be performed by immunoenzymatic-assay, immunofluorescence, fluorescence-activated cell sorter, radioimmunoassay, immunoprecipitative assay or inhibition of biological activity.

The hybridoma cultures selected will exhibit strong binding characteristics to the small moiety (and immunogen compound) and exclude binding with the spacer arm-carrier product and with the carrier itself.

Following the identification of cell cultures producing the desired monoclonal antibodies, subcloning to refine the selected culture can be performed. These techniques are known to those skilled in the art. See for example Goding, James Goding, *Monoclonal Antibodies: Principles and Practice, 2nd Edition, Academic Press, San Diego, Calif.* 1986, the disclosure of which is incorporated herein by reference.

Briefly, the appropriately selected cell culture is separated into one cell units which are then recultured. The subclone cultures are then again tested for specific immunoreactivity, lack of cross-reactivity and the amount of monoclonal antibody secreted. Those subcultures exhibiting the highest amounts of secreted monoclonal antibody are chosen for subsequent pilot development.

Following the foregoing techniques, hybridomas producing monoclonal antibodies to mercury and lead cations have been developed. These perpetual cell lines, designated 1F10 and 5H1 respectively are maintained in culture medium and in frozen medium at liquid nitrogen temperature at the laboratories of Bionebraska.

The immunogenic host for these hybridomas was the BALB/c mouse and the fusion partner was the mouse myeloma cell line P3X63-Ag8.653. Immunizations were accomplished with the immunogen compound formed from KLH, glutathione and the metallic cation functioning as the small moiety in complete Freund's adjuvant.

Methods of Application

According to the invention, the monoclonal antibodies can be used to advantage for detection, neutralization, addition or removal of small moieties from biological inanimate systems. These methods apply to qualitative and quantitative analyses of such embodiments as minute concentrations of toxic metal cations, herbicides, pesticides and toxic small organic molecules in aqueous liquid systems and minute quantities of organic and inorganic molecules in there biological or environmental systems or in such compositions as perfumes, cosmetics, pharmaceuticals, health care products, skin treatment products, pesticides, herbicides, toxic solvents used in the production of semi-conductor and integrated circuit components and production materials for electronic components. In each application, the presence of minute quantities of metallic cations or small organic materials could constitute deleterious contaminants. Their ready and early detection will avoid later production or regulatory set-backs.

Alternatively, the presence of minute quantities of small moieties in certain instances may be desirable. For example, the presence of small organic molecules in food products, cosmetics and perfume and the presence of inorganic moieties in such mixtures as doping materials for semi-conductors and integrated circuits contributes to the properties of the product. Quality control of the presence and concentration of these small moieties is essential for the functioning of the product. The detection methods of the invention enable ready and early measurement of the presence of such moieties and avoid later production or regulatory difficulties.

The small moieties in biological or inanimate systems can also be removed by methods according to the invention. In the main, immobilization of the monoclonal antibodies on a solid support followed by its mixture with the materials of the biological or inanimate system will remove the small moieties. In this instance, the immobilization of the monoclonal antibodies can be accomplished by techniques known to those of skill in the art. See, for example, *Affinity Chromatography*, C. R. Fowe & P. D. G. Sean, John Wiley & Sons, London 1974, the disclosure of which is incorporated herein by reference. Removal is accomplished by passing a fluid mixture of the system ingredients suspected as having the small moieties over the immobilized monoclonal antibodies. Of course, the monoclonal antibodies are designed to be specific for the small moiety sought to be removed.

An advantage of this method is the removal of undesirable small moieties in the presence of similarly structured desirable chemical compounds. For example, whole blood from a patient suffering from mercury poisoning can be removed from the patient, optionally filtered to return the cellular blood components to the patient, and the serum or blood passed over immobilized monoclonal antibodies specific for the mercury. The purified serum or blood can then be returned to the patient. The mercury will be removed but other blood serum components such as zinc, calcium, iron and the like will not.

Likewise, a doping mixture for integrated circuits which contains a trace transition metal can be passed over immobilized monoclonal antibodies which are specific for an undesirable neighboring transition metal. The complexation will remove undesirable trace amounts of similar transition metals and produce an ultrapure doping mixture for the integrated circuit components.

Methods for adding small moieties to biological or inanimate systems focus on the delivery of the small moiety to a particular site. In this instance, the monoclonal antibodies will be bifunctional. The second binding site will be adapted to complex with a selected site within the biological or inanimate system. In this fashion, the monoclonal antibody-small moiety conjugate will deliver the small moiety to a specific site.

This method is particularly suited for heterogenous delivery processes. These processes enable the non-uniform concentration of the small moiety in a system that would otherwise cause its uniform or homogenous distribution. Examples include the delivery of anti-cancer compounds to target organs and tissues within a mammalian system, the delivery of radioactive compounds to specific organs and/or tissues in biological or inanimate systems and the delivery of metallic cations or small organic molecules to specific sites within a system. Fluid or semi-fluid flow of system ingredients would be preferred so that transport of the monoclonal antibody-small moiety conjugate can be rapidly made. The presence of a fluid medium, however, is not an important characteristic. Gels, semi-solidified systems and the like can be employed as long as some semi-fluid connection is present for diffusion of antigen and antibody.

For administration of the monoclonal antibodies to biological systems, the antigenicity of the monoclonal antibodies themselves will preferably be minimized. Use of species-specific cell sources for generation of the hybridomas is an appropriate technique for minimizing the antigenicity of the monoclonal antibodies. Cross-reaction studies of the host and the monoclonal antibody can also be made to determine lack or minimization of monoclonal antibody sensitivity. A preferred means for avoiding adverse immune reaction is the use of the Fab or $F(ab)_2$ fragments of the monoclonal antibodies of this invention. These fragments do not contain the heavy chain tail primarily responsible for such immune reactions and are made by known methods. Their small size and direct carriage of the small moiety allows them easily to pass through or intimately to attach to cellular membranes. They have few bulky groups that would interfere with these processes.

In instances involving in vivo application, the dosage level and routes of monoclonal antibody administration will follow the judgment of the medical practitioner who is in an appropriate position to understand the needs and problems of the patient or mammal. In these situations, the dosage levels of monoclonal antibody compositions being administered will be consonant with the toxicity and sensitivity levels determined for the patient or mammal. The monoclonal antibody compositions will generally be combined for administration with a pharmaceutically acceptable medium such as water, alcohol, buffered aqueous medium, excipients, diluants and the like. Active transport agents can also be included. In general, the processes of administration for removal or addition of small moieties will maintain concentrations as high as possible so that the period for patient intervention is minimized. In each instance, consideration of the physiological characteristics of the small moiety will be important for determining the dosage levels and route of administration.

Specific Applications

A particular application of the present invention contemplates a method for the production of monoclonal antibodies specific for the mercuric cation or another toxic, heavy metal cation. In accordance with this method, the heavy metal cation in question is combined into an immunogen compound as described above and suspended in an aqueous medium. The preferred protein carrier for the immunogen compound in this instance is keyhole limpet hemocyanin. The preferred spacer arm in this instance is an oligopeptide which has sulfhydryl groups capable of coordinating with the heavy metal cation. Glutathione is especially preferred as the spacer arm. The suspension of immunogen compound is used to immunize a host mammal such as a mouse following the techniques outlined above. The laboratory strain of mouse designated BALB/c is particularly preferred.

Antibody-producing cells of the immunized host's spleen are collected and converted into a suspension. These spleen cells are fused with immortal cells as described above. Preferably, myeloma cells of the same animal species as the immunized host are used as the fusion partner. Typically, a cell fusion promoter such as polyethylene glycol is employed to cause formation of the hybridoma cells. The hybridoma cells are diluted and cultured in a medium which does not allow for the growth of unfused cells.

The monoclonal antibodies produced and secreted by the hybridomas are thereafter assayed for the ability to bind immunologically with the heavy metal cations used for immunization. They are further selected for lack of cross-reactivity with carrier and with carrier-spacer arm.

The preferred assay method in this context is an enzyme-linked immunosorbent assay.

The resulting monoclonal antibodies are specific for toxic heavy metal cations and exhibit strong complexation to the heavy metal cations when in the presence of spacer arm, the spacer arm-carrier composition and other similarly structured cations. Preferred monoclonal antibodies are selectively immunoreactive with cations of mercury, lead, cadmium, strontium, nickel, cobalt, gold or arsenic.

According to an embodiment of a method for detecting the presence of toxic heavy metal cations, an immobilized coordinating compound is combined with the unknown mixture containing the toxic heavy metal cation. The heavy metal cation complexes with coordinating compound and is immobilized thereto. Removal of the non-immobilized components leaves a mixture of the immobilized toxic heavy metal cation. Addition of the monoclonal antibody specific for the toxic heavy metal cation forms an immobilized cation-monoclonal antibody complex. Its presence and concentration can be assayed by an ELISA technique or other tagging or visualization technique known to those of skill in the art. In this process, of course, the non-immobilized monoclonal antibody is removed before the assay is conducted.

A kit for quantitatively measuring the presence of a heavy metal cation by the method described above is a further aspect of the invention. The kit will include the immobilized coordination compound, preferably, attached to a solid support such as the well of a microtiter plate or a chromatographic material, and a portion of monoclonal antibody specific for the toxic metal cation in question, wherein the portion is preferably metered into several aliquots of varying, known concentration. A third component of the kit will be the visualization or tagging assay material for determination of the presence of the monoclonal antibody-toxic metal cation complex. If desired, a meter or other device for detecting and signaling the level of visual or other reading from the assay may also be included.

The invention will be further characterized by the following examples. These examples are not meant to limit the scope of the invention which has been fully set forth in the foregoing description. Variation within the concepts of the invention are apparent to those skilled in the art.

EXAMPLE 1

Mercury Cation Monoclonal Antibodies

A. General Procedures

1. Generation of Hybridomas

Hybridoma antibodies have been produced with the spleen cells of BALB/c mouse that had received multiple injections of mercuric ions reacted with glutathione to produce a mercuric ion coordinate covalent compound, which was covalently bound to keyhole limpet hemocyanin ("KLH"). The KLH in complete Freund's adjuvant was utilized to assist in the elicitation of an immune response in the host animal. Glutathione is a three amino acid residue peptide having one reactive sulfhydryl group which forms a coordinate bond with mercuric ions.

Of 134 hybridomas isolated, four were determined to be producing monoclonal antibody specific for glutathione as set forth below in Table 1. In addition, three other hybridomas (1F10, 4A10, and 3E8) were producing monoclonal antibodies that were strongly positive against glutathione-mercuric ions but negative against glutathione without mercuric ions (Table 1.). These three antibodies were subcloned by limiting dilution for further characterization. A fourth antibody (3F5), not included in Table 1, which appeared to be specific for glutathione but bound more tightly in the presence of mercuric ions, was also subcloned.

TABLE I

ELISA Results From Initial Screening of Hybridoma Antibodies Reactive With Glutathione or Glutathione-Mercuric ions

| Hybridoma ions | Glutathione | Glutathione-mercuric |
|---|---|---|
| 1H11 | 1.202 | 1.246 |
| 2A9 | 1.052 | 0.758 |
| 3A12 | 2.127 | 1.792 |
| 3H9 | 2.134 | 1.606 |
| 1F10 | 0.406 | 1.175 |
| 3E8 | 0.410 | 1.076 |
| 4A10 | 0.400 | 1.104 |
| Negative[b] | 0.456 | 0.428 |

[a]Values are the absorbance at 405 nm shown by the specified hybridoma antibody in the ELISA.
[b]The value shown is the average absorbance at 405 nm of six wells on and ELISA plate that received culture fluid containing a monoclonal hybridoma antibody specific for dinitrophenol instead of culture fluid containing a mercuric ion specific monoclonal antibody in the first step of the assay.

Only one positive subclone was obtained from hybridoma 3E8, and it subsequently lost its antibody-secreting ability. Several subclones secreting antibodies that were specific for mercuric ion were isolated from the other mercuric ion-specific hybridomas. The results of the analysis of these subclones and those from 3F5 with BSA-glutathione-mercuric ion and BSA-glutathione are shown in Table 2. All of the frozen hybridoma samples have been thawed from liquid nitrogen and assayed for persistence of antibody secretion after thawing.

TABLE 2

ELISA Results from Hybridoma
Subclones Specific for Glutathione
or Glutathione-Mercuric ions

| Hybridoma | Glutathione | Glutathione-mercuric ion |
| --- | --- | --- |
| 1F10.A6 | 0.289 | 1.048 |
| 1F10.A9 | 0.300 | 0.979 |
| 1F10.A11 | 0.285 | 1.015 |
| 1F10.B1 | 0.302 | 0.861 |
| 1F10.B2 | 0.271 | 0.952 |
| 1F10.E2 | 0.292 | 1.005 |
| 4A10.B4 | 0.322 | 1.279 |
| 3F5.A8 | 0.494 | 0.773 |
| 3F5.B11 | 0.563 | 0.865 |
| 3F5.D5 | 0.658 | 0.884 |
| Negative[b] | 0.332 | 0.295 |

[a]Values are the averages of the absorbance at 405 nm of triplicate samples for each hybridoma subclone in an ELISA.
[b]The value shown is the average absorbance at 405 nm for six wells in an ELISA plate that received culture fluid containing a monoclonal hybridoma antibody specific for dinitrophenol instead of culture fluid containing a mercuric ion-specific monoclonal antibody in the first step of the assay.

Based on this ELISA assay work, hybridomas 1F10 and 4A10 were further evaluated to determine if the antibodies secreted were specific for mercuric ions.

2. Determination of Mercuric-ion Specific Monoclonal Antibodies

Various methods were used to confirm that the antibodies secreted by hybridomas 4A10 and 1F10 were specific to mercuric ions. If the antibody being secreted by these hybridomas were specific, it should be possible to inhibit binding of the antibody to glutathione-mercuric ions by incubation in the presence of various concentrations of mercuric chloride. This competitive inhibition assay was conducted with antibody-containing culture fluids from the parental hybridomas 4A10 and 1F10. The results for inhibition of 1F10 by mercuric chloride and magnesium chloride are shown in FIG. 1.

Figure 1:
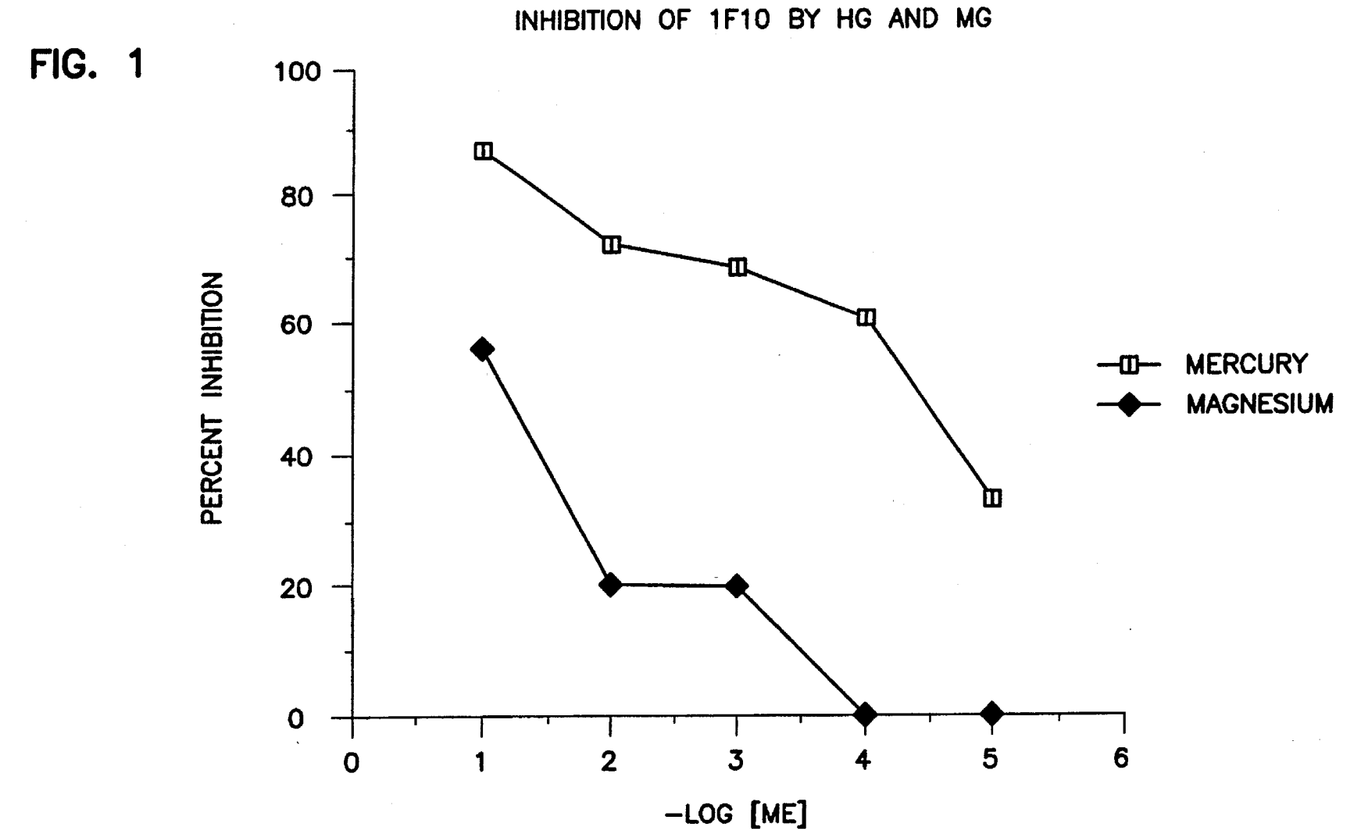
FIG. 1 shows a graph of the results of an immunosorbent assay. The results depict the competitive binding of mercuric ion and magnesium ion for a monoclonal antibody to mercury.

FIG. 1 shows inhibition of binding of antibody secreted by hybridoma designated as 1F10 to immobilized glutathione-mercuric ion by various concentrations of magnesium ions. Metal ions at the indicated concentrations were incubated with culture fluid from the monoclonal antibody in an enzyme-linked immunosorbent assay ("ELISA") plate. The absorbance at 405 nm was determined for each sample, and the percent inhibition of each metal ion concentration was determined by the following formula:

$$\text{Percent inhibition} = \frac{A_{405} \text{ of inhibitor} - A_{405} \text{ of neg. control}}{A_{405} \text{ of pos. control} - A_{405} \text{ of neg. control}}$$

Magnesium chloride at the same concentrations as mercuric chloride was included as a control to rule out the possibility that inhibition could be due to excess amounts of divalent cations or increased ionic strength of the incubation solution. It can be seen that 50% inhibition with mercuric chloride occurs between 0.0001 and 0.00001M, while magnesium chloride approaches 50% inhibition only at the highest concentration.

Therefore, in both enzyme-linked immunosorbent assay (ELISA) and the competitive assay, the monoclonal antibodies were specific for mercuric ions. The preformation of a mercuric ion coordinate covalent complex is not a requirement for monoclonal antibody recognition of mercuric ion. Thus, the monoclonal antibody reacts with free mercuric ions which are independent of coordinating agents.

Figure 2:
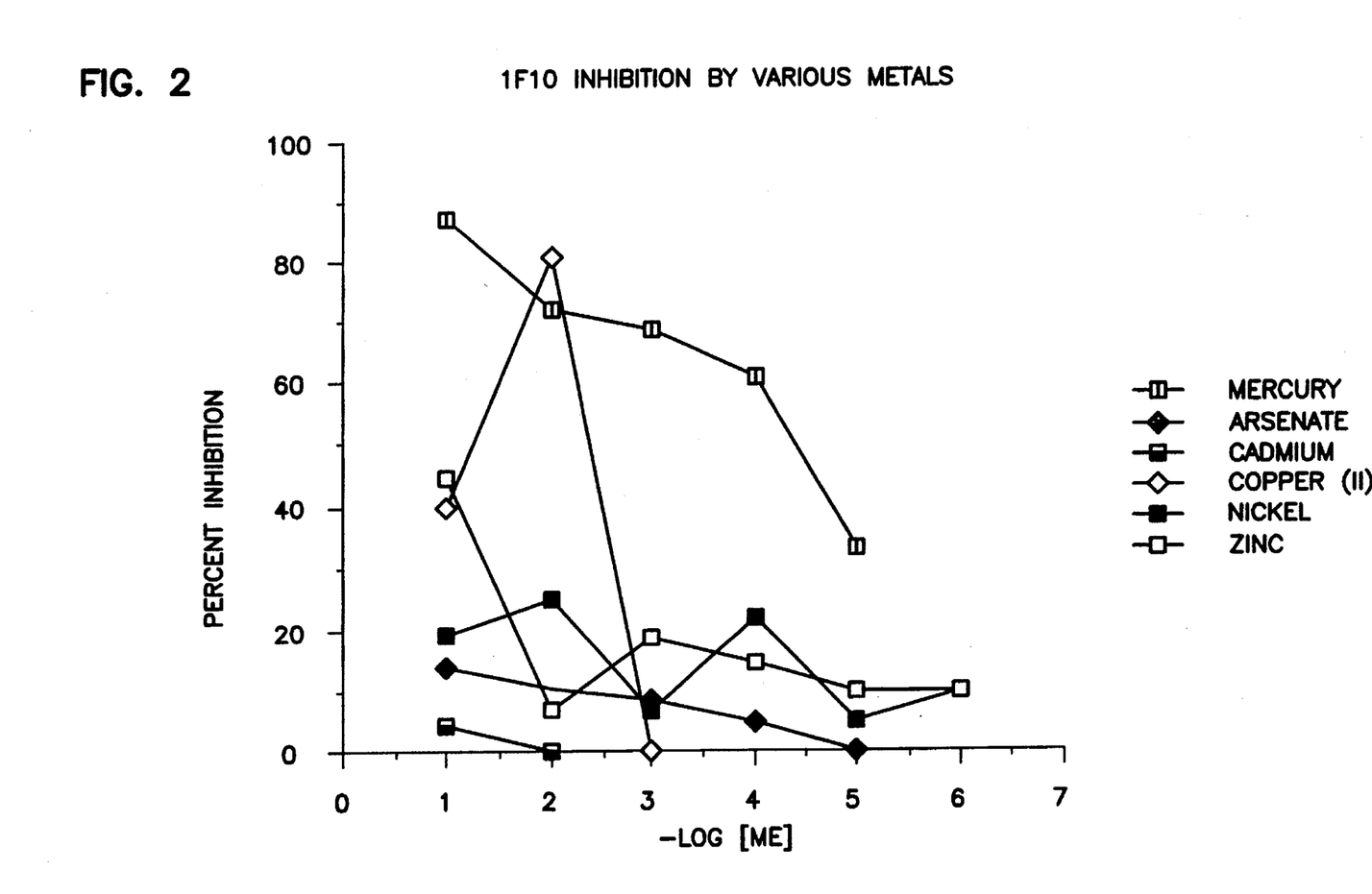
FIG. 2 shows a graph of an immunosorbent assay. The results depict the competitive inhibitory binding of mercury and various divalent cations for a monoclonal antibody to mercury.

Various other metals were assayed for inhibition of binding of the monoclonal antibodies to mercuric ion. The cationic metals assayed include the ions of zinc, copper, cadmium, nickel, and arsenic. The results of these inhibition assays are shown in FIG. 2. To produce these results the binding of monoclonal antibody secreted by the hybridoma designated as 1F10 to immobilized glutathione-mercuric ions by various concentrations of divalent cations was examined. Metal ions at the indicated concentrations were incubated with culture fluid from the antibody in an ELISA plate. The absorbance at 405 nm was determined for each sample, and the percent inhibition of each metal ion concentration was determined by the same formula used for FIG. 1.

However, none of the metals showed a titratable inhibition of monoclonal antibody binding similar to that seen with free mercuric ions. Therefore, based upon the heavy metal ions tested, the monoclonal antibodies produced by immunization with mercuric ions are specific for mercuric ions.

Further analysis shows that the monoclonal antibodies produced are specific for the mercuric ions per se and that glutathione is not needed for the monoclonal antibodies to react with and bind to the mercuric ions. The monoclonal antibody from hybridoma 1F10 was assayed against BSA-glutathione, BSA-glutathione mercuric ions, and BSA-mercuric ions. When compared against a negative control consisting of a monoclonal antibody specific for an unrelated antigen the results show that the monoclonal antibody binds to mercuric ion in the absence of glutathione.

BSA-glutathione adsorbed to the wells of a microliter plate effectively binds mercuric ions from solution and enables detection of mercuric ions in a concentration as low as $10^{-9}$M (0.2 ppb) by the antibody (Table 3) without appreciable loss of sensitivity.

TABLE 3

Assay Utilizing BSA-Glutathione
Added to Polyvinyl Chloride Microtiter Plates

| Hg Conc. (M)[a] | A405 |
| --- | --- |
| $10^{-1}$[b] | 0.442 |
| $10^{-2}$ | 1.213 |
| $10^{-3}$ | 1.453 |
| $10^{-4}$ | 0.936 |
| $10^{-5}$ | 1.364 |
| $10^{-6}$ | 0.962 |
| $10^{-7}$ | 1.113 |
| $10^{-8}$ | 1.113 |
| $10^{-9}$ | 1.107 |
| 0 | 0.394 |

[a]Mercuric ion concentration refers to the concentration of mercuric chloride in the PBS added to the well to which BSA-glutathione had been absorbed.
[b]The absorbance at concentrations of $10^{-1}$ M is only slightly higher than the control because the large numbers of ions present creates a substantial amount of stearic hindrance which prevents binding and is not evidence of any lack of specificity of the monoclonal antibody.

Figure 3:
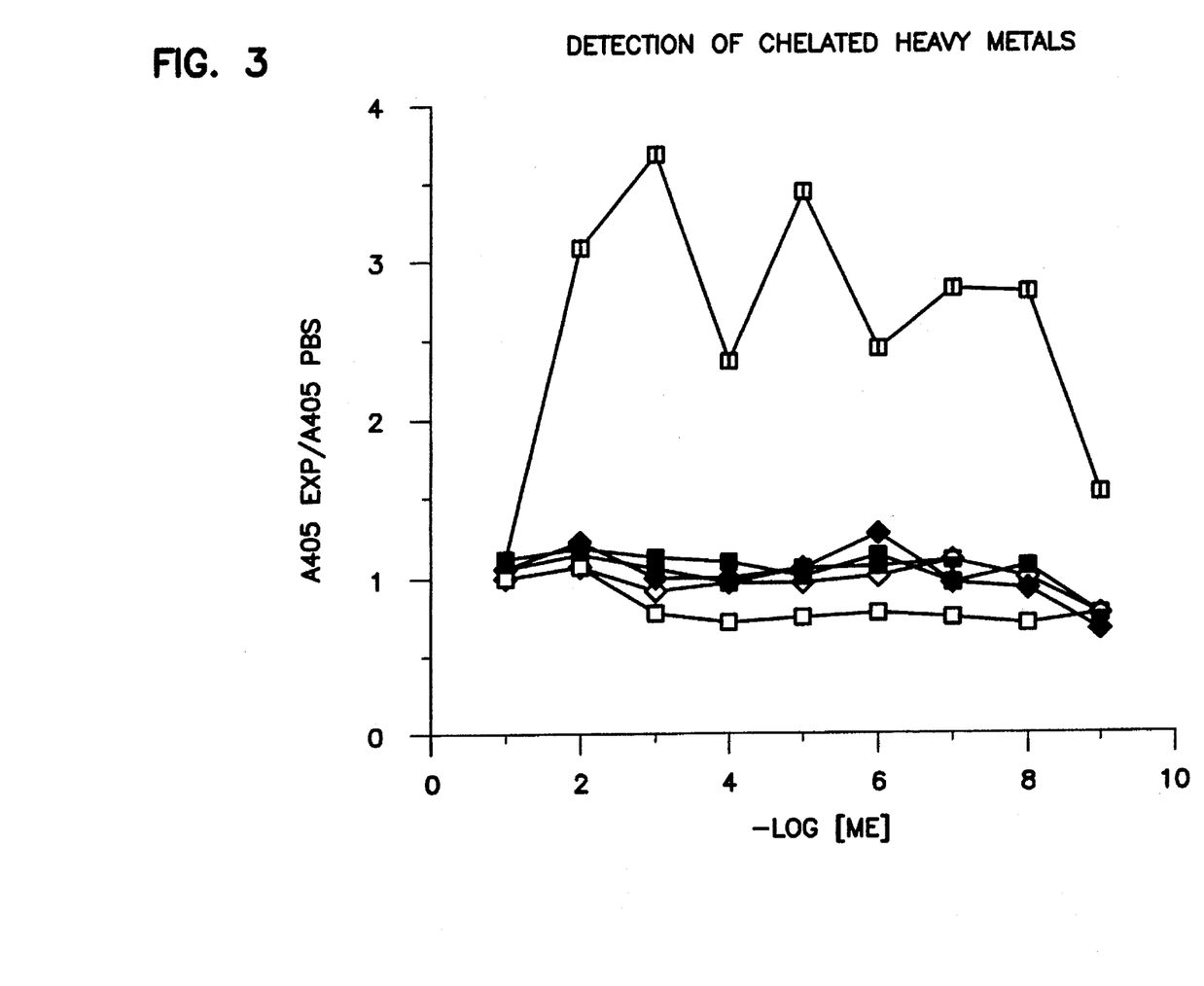
FIG. 3 is a graph of the results of an immunosorbent assay of the binding of a monoclonal antibody to several heavy metal ions. The monoclonal antibody is specific for mercuric cations.

The specificity of the antibody reactivity for mercuric ion is shown in FIG. 3. Here the reactions of various coordinated heavy metal ions with the monoclonal antibody secreted by the hybridoma designated 1F10 indicate that it is specific for mercuric ions.

Phosphate-buffered saline ("PBS") containing metal ions at the indicated concentrations was added to triplicate microtiter wells to which BSA-glutathione had been absorbed. After incubation at room temperature for 30 minutes, the plates were washed to remove unbound metals, and the plates were used for the standard ELISA to detect mercuric ions. In this experiment various heavy metal ions at the indicated concentrations were added to microtiter plates to which BSA-glutathione had been adsorbed. The PBS containing the metal ions was allowed to incubate at room temperature for 30 minutes, and the plates were then used in an ELISA to determine whether the monoclonal antibody would react with the bound metal. The data in FIG. 3 show that mercuric ion is the only heavy metal ion which demonstrates a reasonable increase in absorbance.

B. Particular Preparations

1. Linkage of Mercuric Ions to Protein Carriers

To prepare antigen for injection and immunoassay, 136 mg $HgCl_2$ (400 umoles), 61 mg glutathione (200 umoles) and 54 mg NaCl were dissolved in 10 ml of water. Thirty milliliters of cold ethanol were added and incubated for 30 minutes at 0°C. The reaction mixture was centrifuged at 10,000 g for 30 minutes, and the pellet was washed with 30 ml of cold ethanol. The pellet was dissolved in 200 ml of 40% dimethylformamide pH 4.8, containing 200 mg of 1-ethyl-3-(3-dimethylaminopropyl)-carbodiimide, and 1 g of either bovine serum albumin or keyhole limpet hemocyanin were added to the solution. The reaction mixture was stirred at room temperature overnight. The mixture was then centrifuged as above, resuspended in PBS, and dialyzed overnight at 4° C. against 4 liters of PBS.

2. Immunization of BALB/c Mice

BALB/c mice received multiple injections of the antigen prepared with 10 ug of protein per injection. The antigen was mercuric ion-glutathione-KLH emulsified in Freund's adjuvant. Complete adjuvant was used for the first two injections, while incomplete adjuvant was used for all subsequent injections. After the fourth injection, a drop of blood from the tail of each mouse was collected separately in 0.5 ml of PBS, and each sample was assayed by ELISA for the presence of antigen-specific antibody. The mice used for hybridoma production received an intraperitoneal injection consisting of 10 ug of antigen in PBS 3–4 days before cell fusion.

3. Hybridoma Production

The spleen was removed aseptically from a mouse, and the cells were isolated by placing the spleen in 5 ml of sterile PBS and teasing it with two sterile, 18-gauge hypodermic needles. The cell suspension was added to an empty sterile, conical, 15-ml centrifuge tube and tissue fragments were allowed to settle for 1–2 minutes. The cells still in suspension were placed in a tube similar to that above and centrifuged at 300 g for 10 minutes at room temperature. The cells were then washed 3 times by centrifugation in serum-free DMEM (Dulbecco's modified Eagle's medium). Spleen cells were co-pelleted with P3X63-Ag8.653 myeloma cells at a ratio of 4 spleen cells to 1 myeloma cell. The supernatant fluid was removed, and the pellet was suspended in 1 ml of 35% polyethylene glycol for 1 minute. The polyethylene glycol was gradually diluted by addition of increasing amounts of serum-free DMEM over a period of 15 minutes. The cells were then suspended in HAT medium (*Monoclonal Antibodies*, Kennett, McKean, Backitt, eds. Plenum press 1981) at a concentration of $2\times10^5$ myeloma cells per ml, and 4 drops from a 5-ml pipet were added to each well of 5 96-well microtiter plates. The plates were incubated in 10% $CO_2$ at 37° C. for one week. At that time half of the culture fluid was withdrawn from each well and replaced by 2 drops of fresh HT medium (HAT medium without aminopterin), and the plates were incubated as above for another week. Then, approximately 100 ul of culture fluid was taken from each well containing macroscopically visible cell growth, and the ELISA technique described infra was used for identification of those culture fluids containing mercuric ion-specific antibodies.

4. Enzyme-Linked Immunosorbent Assay (ELISA)

Polyvinyl chloride microtiter assay plates were coated with antigen by addition of 50 ul of mercuric ion-glutathione-BSA or glutathione-BSA at a concentration of 5 ug/ml in PBS to each well of the plate. The plates were allowed to incubate at room temperature overnight to allow the antigen to dry on the plate. Next day the plates were blocked by addition of 200 ul of 5% nonfat dry milk in PBS to each well; the addition of the dry milk blocked the remaining protein-binding sites. The plates were incubated for 2 hours at room temperature, then washed 3 times with ELISA wash (PBS with 0.1% of nonidet P-40).

Fifty microliters of culture fluid being assayed for the presence of antigen-specific antibody were added to the appropriate well, and the plates were incubated at room temperature for 2 hours. The plates were again washed 3 times with ELISA wash, and 50 ul of goat anti-mouse serum (Cooper Biomedical) diluted 1:1000 in 2% BSA in PBS were added to each well. After incubation and washing as above, 50 ul of rabbit anti-goat serum conjugated to alkaline phosphatase (Sigma) diluted 1:1000 in 50 mM Tris-HCl, pH 8.0, containing 1 mM $MgCl_2$, 5% BSA and 0.04% $NaN_3$, were added to each well. After being incubated and washed as above, 150 ul of phosphatase substrate (0.4 mM dinitrophenol phosphate in 1M diethanolamine, pH 9.8, containing 25 mM $MgCl_2$) were added to each well.

The enzyme catalyzed conversion of dinitrophenol phosphate to dinitrophenol was allowed to proceed at room temperature for 30–60 minutes. The absorbance of each well at 405 nm (dinitrophenol) was measured with a UV spectrometer.

The use of other enzymes as sensors is also possible provided that such enzymes can be linked to an appropriate antibody, and catalyze a reaction which produces a color change. For example, beta galactosidase, urease, or horseradish peroxidase could be utilized in this context.

5. Inhibition of Binding of Mercuric ion-Specific Antibody by Metals

Microtiter assay plates containing mercuric ion-glutathione-BSA were prepared as described above. After blocking the plates with non-fat dry milk, 25 ul of a solution containing a known concentration of the metal to be assayed were added to each of triplicate wells of the plate, along with 25 ul of culture fluid containing mercury-specific antibody. The concentrations of metal ranged from $2\times10^{-1}$M to $2\times10^{-6}$M, so the final concentration of metal in the wells ranged from $10^{-1}$M to $10^{-6}$M. The plates were incubated for 30 minutes at room temperature, washed with ELISA wash as above, and then assayed using the ELISA technique as described above. The absorbance at 405 nm was measured for each well, and the percent inhibition of antibody binding for each concentration of metal was calculated according to the following formula:

$$\text{Percent inhibition} = \frac{A_{405} \text{ of inhibitor} - A_{405} \text{ of neg. control}}{A_{405} \text{ of pos. control} - A_{405} \text{ of neg. control}}$$

The negative control measured the binding of a dinitrophenol specific antibody to the antigen mentioned above in the presence of the corresponding metal ions. The positive control consisted of triplicate wells that contained 25 ul of mercuric ion-specific antibody and 25 ul of PBS with no metal.

6. Binding of Mercuric ions to Immobilized Coordinating Spacer Arms

One hundred microliters of BSA-glutathione at a concentration of 5 ug/ml were added to the wells of a microtiter plate and allowed to dry overnight. The plates were then blocked with nonfat dry milk as above. One hundred microliters of PBS containing a known concentration of the metal ion to be assayed were added to triplicate wells on the plate, which was then incubated at room temperature for 30 minutes. After this incubation period the plates were washed with ELISA wash to remove unbound metal ions and then used in the standard ELISA to measure reactivity with the mercuric ion-specific antibody.

7. Assay of Mercuric Ion-Specific Antibody Against BSA Glutathione, BSA Glutathione-Mercury and BSA-Mercury Mercuric ion specific antibody secreted from hybridoma 1F10 was assayed against BSA-glutathione, BSA-glutathione-mercury and BSA-mercuric ions. The results set forth below are the average absorbance plus the standard deviation of nine individual samples assayed against the three antigens.

| Antigen | 1F10.All | Neg. Control |
|---|---|---|
| BSA-glutathione | 0.418 ± 0.014 | 0.419 ± 0.061 |
| BSA-glutathione-mercuric ion | 3.144 ± 0.132 | 0.171 ± 0.042 |
| BSA-mercuric ion | 2.861 ± 0.092 | 0.223 ± 0.027 |

EXAMPLE 2

Lead Cation Monoclonal Antibodies

Pursuant to the procedures (part A) to generate hybridomas, and to make particular preparations (part B) given in Example 1, monoclonal antibodies to lead cation were produced. The following substitutions in those procedures and preparations were made:

A1) Generation of Hybridomas; lead cations instead of mercuric ion were used; 100 hybridomas were isolated; one showed specific lead cation reactivity.

A2) Determination of Specific Monoclonal Antibodies not conducted.

B1) Linkage; 400 umoles of lead chloride was substituted for the mercuric chloride.

B2) Immunization; The antigen was lead cation glutathione-KLH.

B3) Hybridoma Production; The same procedure was used.

B4) Assay

Polyvinyl chloride-microtiter assay plates were coated with antigen by addition of 50 ul of lead cation glutathione-BSA or glutathione-BSA at a concentration of 5 ug/ml in PBS to each well of the plate. The plates were allowed to incubate at room temperature overnight to allow the antigen to dry on the plate. Next day the plates were blocked by addition of 200 ul of 5% nonfat dry milk in PBS to each well; the addition of the dry milk blocked the remaining protein-binding sites. The plates were incubated for 2 hours at room temperature, then washed 3 times with ELISA wash (PBS with 0.1% of nonidet P-40).

Fifty microliters of culture fluid being assayed for the presence of antigen-specific antibody were added to the appropriate well, and the plates were incubated at room temperature for 2 hours. The plates were again washed 3 times with ELISA wash, and 50 ul of goat anti-mouse serum (Cooper Biomedical) diluted 1:1000 in 2% BSA in PBS were added to each well. After incubation and washing as above, 50 ul of rabbit anti-goat serum conjugated to alkaline phosphatase (Sigma) diluted 1:1000 in 50 mM Tris-HCl, pH 8.0, containing 1 mM $MgCl_2$, 5% BSA and 0.04% $NaN_3$, were added to each well. After being incubated and washed as above, 150 ul of phosphatase substrate (0.4 mM dinitrophenol phosphate in 1M diethanolamine, pH 9.8, containing 25 mM $MgCl_2$) were added to each well.

The enzyme catalyzed conversion of dinitrophenol phosphate to dinitrophenol was allowed to proceed at room temperature for 30–60 minutes. The absorbance of each well at 405 nm (dinitrophenol) was measured with a UV spectrometer.

The use of other enzymes as sensors is also possible provided that such enzymes can be linked to an appropriate antibody, and catalyze a reaction which produces a color change. For example, beta galactosidase urease, or horseradish peroxidase could be utilized in this context.

These measurements indicated that hybridoma 5H1, produced monoclonal antibodies that were strongly positive against glutathione-lead cation but were negative against glutathione alone.

EXAMPLE 3

Experimental Procedure for Organic Small Moiety

1. Linkage of Trichloroethylene Mimic to Protein Carrier

To prepare antigen for injection and immunoassay, 136 (400 umoles) of N-(trichloroacryloyl)glycine and 54 mg NaCl can be dissolved in 200 ml of 40% dimethylformanide pH 4.8, containing 200 mg of 1-ethyl-3-(3-dimethylaminopropyl)-carbodiimide, and 1 g of either bovine serum albumin or keyhole limpet hemocyanin. The reaction mixture can be stirred at room temperature overnight. The mixture may then be centrifuged resuspended in PBS, and can be dialyzed overnight at 4° C. against 4 liters of PBS.

2. Immunization of BALB/c Mice

BALB/c mice can receive multiple injections of the foregoing antigen prepared with 10 ug of protein per injection. After the fourth injection, a drop of blood from the tail of each mouse can be collected separately in 0.5 ml of PBS, and each sample can be assayed by ELISA for the presence of antigen-specific antibody. The mice to be used for hybridoma production can receive an intraperitoneal injection consisting of 10 ug of antigen in PBS 3–4 days before cell fusion.

3. Hybridoma Production

The spleen can be removed aseptically from a mouse, and the cells isolated as described above. Spleen cells can be co-pelleted with P3X63-Ag8.653 myeloma cells at a ratio of 4 spleen cells to 1 myeloma cell. The supernatant fluid can be removed, and the pellet suspended in 1 ml of 35% polyethylene glycol for 1 minute. The polyethylene glycol can be gradually diluted by addition of increasing amounts of serum-free DMEM over a period of 15 minutes. The cells can be then suspended in HAT medium (*Monoclonal Antibodies*, Kennett, McKean, Backitt, eds. Plenum Press 1981) at a concentration of $2\times10^5$ myeloma cells per ml; and 4 drops from a 5-ml pipet can be added to each well of 5 96-well microtiter plates. The plates can be incubated as described above. Approximately 100 ul of culture fluid can be taken from each well containing macroscopically visible cell growth, and the ELISA technique described above can be used for identification of those desirable culture fluids.

4. Enzyme-Linked Immunosorbent Assay (ELISA)

Polyvinyl chloride microtiter assay plates can be coated with antigen by addition of 50 ul of N-(trichloroacryloyl)-glycine-BSA or glycine BSA at a concentration of 5 ug/ml in PBS to each well of the plate. The plates can be incubated and prepared for ELISA assay as described above.

Fifty microliters of culture fluid being assayed for the presence of antigen-specific antibody can added to the appropriate well, and the plates can be incubated at room temperature for 2 hours. The plates can again be washed with ELISA wash, and 50 ul of goat anti-mouse serum (Cooper Biomedical) diluted 1:1000 in 2% BSA in PBS can be added to each well. After incubation and washing as above, 50 ul of rabbit anti-goat serum conjugated to alkaline phosphatase (Sigma) diluted 1:1000 in 50 mM Tris-HCl, pH 8.0, containing 1 mM $MgCl_2$, and 0.04% $NaN_3$, can be added to each well. After being incubated and washed as above, 150 ul of phosphatase substrate (0.4 mM dinitrophenol phosphate in 1M diethanolamine, pH 9.8, containing 25 mM $Mg_2$ Cl) can be added to each well.

The enzyme-catalyzed conversion of dinitrophenol phosphate to dinitrophenol may be allowed to proceed at room temperature for a sufficient time. Then, the absorbance of each well at 405 nm (dinitrophenol) can be measured with a spectrophotometer. Appropriate absorbance from the wells containing immunogen compound and lack of absorbance from corresponding wells containing carrier will select the desired culture fluid and hybridoma.

Assay for Trichloroethylene in Water

Microtiter assay plates coated with a constant amount of immobilized monoclonal antibody from the foregoing selected hybridoma can be prepared by the technique of L. Wide and J. Porath, *Biochem. Biophys. Act A*, 130: 257–260 (1966). Briefly, this technique will involve addition of 50 μl of metal-specific antibody (20 mg/ml in PBS) to each well of a microtiter plate. The plate will be inovated for 2 nrs, washed with PBS, and blocked for 2 hrs. with 5% nonfat dry milk. The plates can then be saturated with radioactive trichloroethylene ($^{14}C$ or $^3H$). The plates can be incubated for a sufficient time, about 1 hour and then washed with the ELISA wash described above. Addition of aliquots of water containing an unknown concentration of trichloroethylene can then be added to the assay plate wells. After incubating for a sufficient time, e.g. about 1, hour, the fluids from each of the wells can be removed and counted in a scintillation counter. A comparison of the counts with a standard curve constructed from data produced by tests on known concentrations of trichloroethylene will yield the concentration of unknown in the test sample.

We claim:

1. A method for detecting a metallic cation in liquid medium which comprises:

adding a portion of the liquid medium containing the metallic cation to an immobilizing coordinating compound to produce a coordinated immobilized cation mixture;

combining the coordinated immobilized cation mixture and an excess of a monoclonal antibody which is immunoreactive with a bare metal cation to form a complexed mixture containing the immobilized monoclonal antibody-metallic cation complex;

removing non-immobilized materials from the complexed mixture; and conducting the immunoassay for the immobilized monoclonal antibody in the complexed mixture to determine the amount of immobilized monoclonal antibody-metallic cation complex present; wherein, the immobilizing coordinating compound has at least one metallic cation Lewis base coordination site arranged at one end so that the metallic cation is maintained in at least a partially exposed state and complete inclusion or chelation of the metallic cation by the immobilizing coordinating compound is prevented.

2. A method for detecting a metallic cation in a liquid, which comprises:

saturating a known first amount of an immobilized monoclonal antibody with a known amount of radioactive metallic cation to form a mixture containing a radioactive, immobilized monoclonal antibody-metallic cation complex;

removing all uncomplexed components from the mixture;

adding an aliquot of an unknown second amount of the metallic cation to the mixture and allowing the resulting reaction to equilibrated; and determining the concentration of unknown second amount of the metallic cation by measuring the amount of radioactive metallic cation in solution after equilibration; wherein, the monoclonal antibody is immunoreactive with the bare metallic cation.

3. A method according to claim 1, wherein the monoclonal antibody is specific for a metallic cation of mercury, lead or chromium.

4. A method for detecting the presence of a specific heavy metal cation in an aqueous medium which comprises:

adding an oligopeptide having reactive sulfhydryl groups to an aliquot of the aqueous medium containing the heavy metal cation to form a coordinate complex of the oligopeptide and the heavy metal cation;

immobilizing the coordinate complex to form an immobilized system;

adding an aliquot of a monoclonal antibody that is specific for the heavy metal cation to the immobilized system to form a test mixture with an immobilized monoclonal antibody-specific heavy metal cation complex;

removing all non-immobilized material from the test mixture; and conducting an immunoassay of the monoclonal antibody in the immobilized antibody-specific heavy metal cation complex to determine the amount of specific heavy metal cation in the aliquot; wherein, the monoclonal antibody is immunoreactive with the bare metallic cation.

5. The method of claim 4 wherein said metal ion is mercuric ion.

6. The method according to claim 4 wherein said oligopeptide is glutathione.

7. The method of claim 4 wherein the determination is accomplished by an enzyme-linked immunosorbent assay.

8. A method according to claim 1 wherein the immunoassay is a radioactive assay, a visualization assay or an enzyme linked immunosorbent assay.

9. A method according to claim 4 wherein the aqueous medium contains several heavy metal cations in addition to the specific heavy metal cation and the oligopeptide forms coordinate complexes with all heavy metal cation in the aqueous medium and all oligopeptide coordinate complexes are immobilized.

10. A monoclonal antibody which is immunoreactive with a bare metallic cation and with the metallic cation portion of a metallic cation containing complex and which is produced by a hybridoma of myeloma immortal cells and mammalian immune cells sensitized against an immunogen compound;

the immunogen compound being composed of a protein carrier, a spacer arm covalently bonded to the carrier and the metallic cation coordinated in at least a substantially exposed state which the spacer arm such that complete inclusion or chelation of the metallic cation by the spacer arm or the carrier or both is prevented;

the spacer arm having at least one metallic cation coordination site arranged to maintain the metallic cation in at least the substantially exposed state; and the metallic cation being other than an ubiquitous physiological component of the mammal producing the mammalian immune cells, wherein the monoclonal antibody is substantially non-crossreactive with the carrier or spacer arm.

11. A monoclonal antibody according to claim 1 wherein the metallic cation is derived from a metal selected from the group consisting of period 4 transition metals and period 5, 6 and 7 metals, transition elements and inner transition elements.

12. A monoclonal antibody according to claim 1, wherein the carrier is KLH or BSA, the spacer arm is an oligopeptide with sulfhydryl groups and the metallic cation is a cation selected from the group consisting of mercury, lead, cadmium, cobalt, arsenic, and chromium.

13. A monoclonal antibody according to claim 12 wherein the spacer arm is glutathione.

14. A monoclonal antibody according to claim 12 wherein the metallic cation is lead.

15. A monoclonal antibody according to claim 1 wherein the metallic cation is a mercury cation.

16. A monoclonal antibody according to claim 1 having an association constant for the metallic cation that is at least about 10,000 folder greater than its association constant for the carrier-spacer arm compound.

17. A hybridoma of myeloma immortal cells and mammalian immune cells from a mammal previously immunized with an immunogen compound, wherein;

the hybridoma produces a monoclonal antibody which immunoreacts with a metallic cation and with the metallic cation portion of a metallic cation containing complex;

the immunogen compound is composed of a protein carrier, a spacer arm covalently bonded to the carrier and the metallic cation coordinated in a substantially exposed state with the spacer arm such that complete inclusion or chelation of the metallic cation by the spacer arm or the carrier or both is prevented; and the spacer arm has at least one metallic cation coordination site arranged to maintain the metallic cation in at least the substantially exposed state and wherein the metallic cation is other than an ubiquitous physiological component of the mammal producing the mammalian immune cells.

18. A hybridoma according to claim 17 which produces a monoclonal antibody which immunoreacts with a bare metallic cation and lacks substantial immunoreactivity toward the corresponding carrier-spacer arm compound.

19. A hybridoma according to claim 17 wherein the metallic cation is a metal selected from the group consisting of period 4 transition metals and period 5, 6 and 7 metals, transition elements and inner transition elements.

20. A hybridoma according to claim 17 wherein the monoclonal antibody produced thereby specifically immunoreacts with a metallic cation selected from the group consisting of mercury, lead, cadmium, arsenic, or chromium.

21. An isolated monoclonal antibody immunoreactive with a bare metallic cation selected from the group of metallic cations consisting of mercury, lead, cadmium, cobalt, gold, zinc and arsenic, the antibody being capable of immunoreacting with an immunogen, the immunogen having a protein carrier, a spacer arm covalently bonded to the carrier and the metallic cation coordinated in at least a substantially exposed state with the spacer arm such that complete inclusion or chelation of the metallic cation by the spacer arm or carrier or both is prevented, and the antibody having an association constant for the metallic cation that is at least 10,000-fold greater than the association constant for the carrier-spacer arm compound and than the association constant for the other metallic cations of the group.

22. An isolated monoclonal antibody specific for a bare metallic cation selected from the group of metallic cations consisting of mercury, lead, cadmium, zinc cobalt, gold, and arsenic, wherein the antibody lacks substantial cross reactivity with the other metallic cations of the group.

23. A monoclonal antibody according to claim 22, wherein the metallic cation is mercury.

24. A monoclonal antibody according to claim 22, wherein the metallic cation is lead.

25. An isolated monoclonal antibody specific for a metallic cation of mercury, lead or chromium.

26. An isolated monoclonal antibody specific for a metallic cation of nickel, wherein the antibody lacks substantial crossreactivity with other metal cations.

27. An isolated monoclonal antibody specific for a metallic cation of strontium, wherein the antibody lacks substantial crossreactivity with other metal cations.

28. An isolated monoclonal antibody specific for a metallic cation of platinum, wherein the antibody lacks substantial crossreactivity with other metal cations.

* * * * *